(12) United States Patent
Ohara et al.

(10) Patent No.: US 6,471,654 B2
(45) Date of Patent: Oct. 29, 2002

(54) ULTRASONIC ENDOSCOPE

(75) Inventors: Kenichi Ohara, Gunma (JP); Toshiyuki Hashiyama, Saitama (JP)

(73) Assignee: Asahi Kogaku Kogyo Kabushiki Kaisha, Tokyo (JP)

(*) Notice: Subject to any disclaimer, the term of this patent is extended or adjusted under 35 U.S.C. 154(b) by 7 days.

(21) Appl. No.: 09/850,230

(22) Filed: May 8, 2001

(65) Prior Publication Data

US 2001/0041840 A1 Nov. 15, 2001

(30) Foreign Application Priority Data

May 10, 2000 (JP) ........................................ 2000-136734
May 10, 2000 (JP) ........................................ 2000-136735

(51) Int. Cl.[7] ............................................... A61B 8/12
(52) U.S. Cl. ......................................... 600/463; 600/130
(58) Field of Search ............................... 600/110, 128, 600/130, 462–470

(56) References Cited

U.S. PATENT DOCUMENTS

| 5,176,140 A | * | 1/1993 | Kami et al. ............... 600/463 |
| 5,240,003 A | * | 8/1993 | Lancee et al. ............. 310/162 |
| 5,398,689 A | * | 3/1995 | Connor et al. ............. 600/463 |
| 5,685,311 A | * | 11/1997 | Hara ......................... 600/463 |
| 5,876,427 A | * | 3/1999 | Chen et al. ................. 607/88 |
| 5,947,905 A | * | 9/1999 | Hadjicostis et al. ....... 600/463 |
| 6,066,096 A | * | 5/2000 | Smith et al. ............... 600/439 |
| 6,095,970 A | | 8/2000 | Hidaka et al. |

FOREIGN PATENT DOCUMENTS

JP  2-265534  10/1990

* cited by examiner

Primary Examiner—Francis J. Jaworski
(74) Attorney, Agent, or Firm—Greenblum & Bernstein, P.L.C.

(57) ABSTRACT

In an ultrasonic endoscope, a plurality of flexible substrates are connected to an ultrasonic probe as a signal transmission member for transmitting a signal which is inputted into/outputted from the ultrasonic probe. The plurality of flexible substrates are drawn into a curved portion and connected to a signal cable at lengthwise different positions respectively in the inside of a flexible tube portion.

10 Claims, 11 Drawing Sheets

FIG. 11
FIG. 12
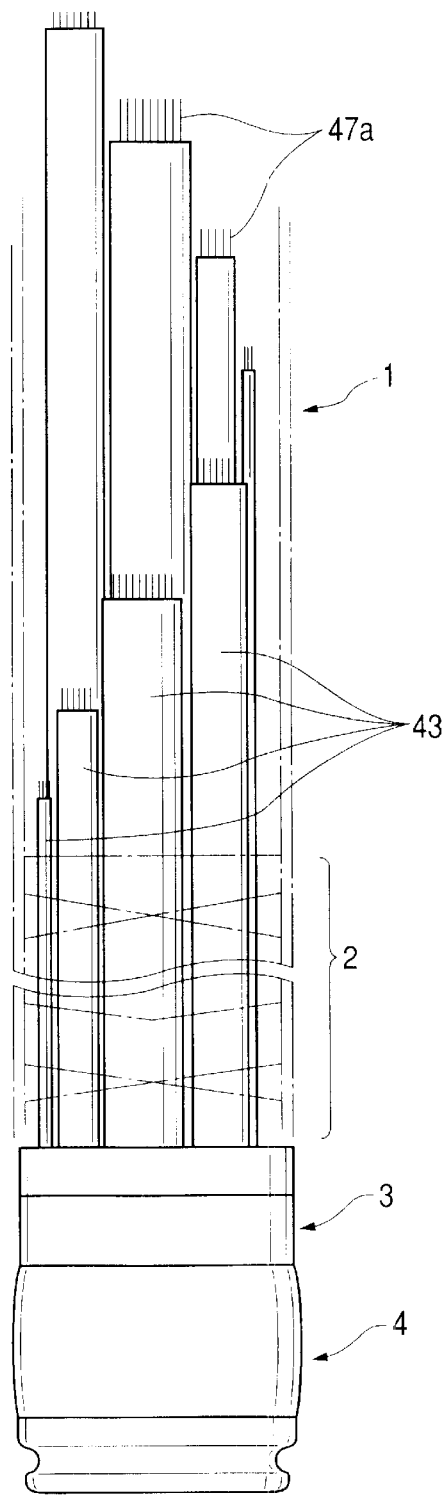
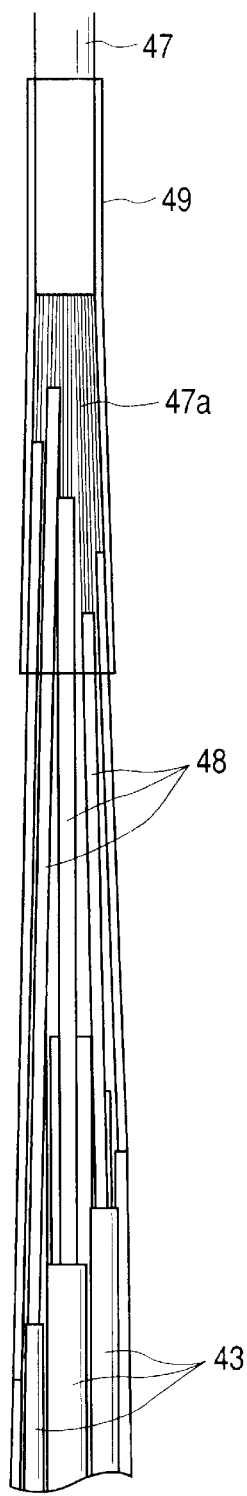

ULTRASONIC ENDOSCOPE

BACKGROUND OF THE INVENTION

The present invention relates to an ultrasonic endoscope having an ultrasonic probe and an optical observation objective optical system which are provided side by side at a forward end of an insertion portion.

In an ultrasonic endoscope, a signal transmission member for transmitting a signal input into/output from an ultrasonic probe needs to be disposed in an insertion portion so as to be inserted into the insertion portion. Generally, a signal cable having a large number of signal wires bound up into one is used as the signal transmission member.

The signal cable, however, gave limitation to arrangement of other inclusions because the signal cable occupied a large lumped section in the insertion portion. Particularly in a portion (curved portion) adjacent to a forward end of the insertion portion small in the degree of freedom of arrangement, the signal cable was apt to interfere with the other inclusions. Therefore, the diameter of the adjacent portion must be enlarged, so that characteristic for insertion into a body cavity was worsened. Hence, such an ultrasonic endoscope gave intensive pain to a patient into whom the ultrasonic endoscope was inserted, compared with a general endoscope.

SUMMARY OF THE INVENTION

Therefore, an object of the present invention is to provide an ultrasonic endoscope in which an inner space near a forward end of an insertion portion is used so effectively that a signal transmission member can be disposed so as to be inserted into the inner space and that improvement of insertion characteristic can be attained by reduction in the outer diameter of the insertion portion.

In order to achieve the above object, according to the present invention, there is provided an ultrasonic endoscope comprising a flexible tube portion forming an insertion portion, a curved portion connected to a forward end of the flexible tube portion so as to be bent by remote control, an ultrasonic probe for transmitting and receiving an ultrasonic signal, and an objective optical system for making optical observation, the probe and the objective optical system being disposed in a further forward position than the curved portion, wherein a plurality of flexible substrates are connected to the ultrasonic probe as a signal transmission member for transmitting a signal which is inputted into/outputted from the ultrasonic probe, the plurality of flexible substrates being drawn into the curved portion and connected to a signal cable at lengthwise different positions respectively in the inside of the flexible tube portion.

Incidentally, the plurality of flexible substrates may be arranged in the inside of the curved portion so as to be shaped like a circular arc surrounding other inclusions.

In order to achieve the above object, according to the present invention, there is provided an ultrasonic endoscope comprising a flexible tube portion forming an insertion portion, a curved portion connected to a forward end of the flexible tube portion so as to be bent by remote control, an ultrasonic probe for transmitting and receiving an ultrasonic signal, and an objective optical system for making optical observation, the probe and the objective optical system being disposed in a further forward position than the curved portion, wherein a signal cable including signal wires and disposed so as to be inserted into the flexible tube portion is connected to the ultrasonic probe by a plurality of flexible substrates disposed side by side so as to pass through the inside of the curved portion, and a plurality of signal wires connected to one and the same flexible substrate, among the signal wires drawn out from the signal cable, are bound up into one as a bundle in the connection portion between the flexible substrates and the signal cable.

Incidentally, each of the bundles of the signal wires may be made by being coated with a flexible tube, and the bundles of signal wires may be formed by displacement from one another in an axial direction.

The present disclosure relates to the subject matter contained in Japanese patent application Nos. 2000-136734 and 2000-136735 (both filed on May 10, 2000), which are expressly incorporated herein by reference in their entireties.

BRIEF DESCRIPTION OF THE DRAWINGS

FIG. 11 is a schematic view showing a state of backward end portions of the flexible substrates in the embodiment of the present invention.

FIG. 12 is a side view of portions of connection of the flexible substrates to a signal cable in the embodiment of the present invention.

DESCRIPTION OF THE PREFERRED EMBODIMENT

An embodiment of the present invention will be described below with reference to the accompanied drawings.

Figure 2:
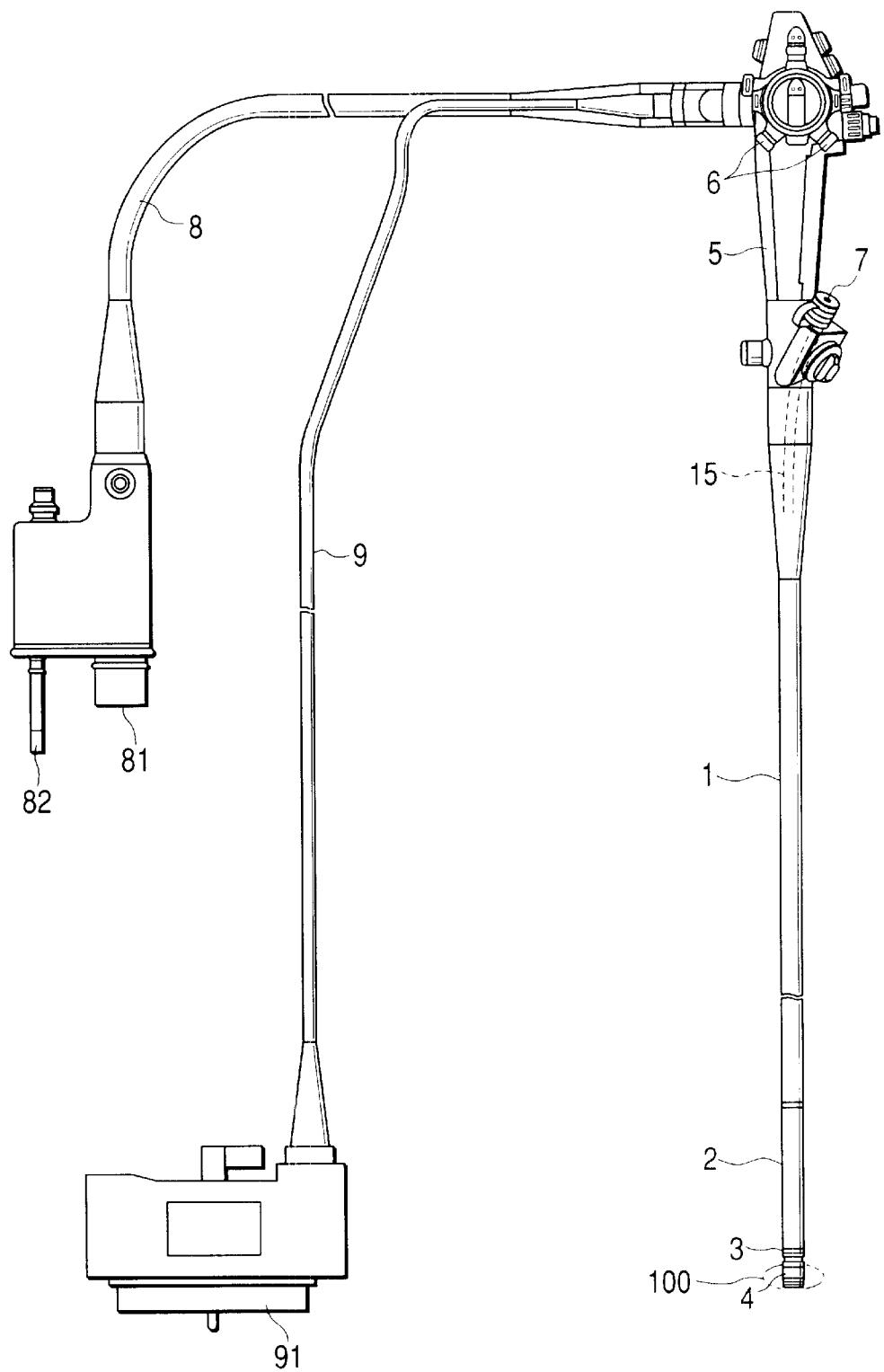
FIG. 2 is a side view showing the overall configuration of the ultrasonic endoscope according to the embodiment of the present invention.

FIG. 2 shows an ultrasonic endoscope which comprises a flexible tube portion 1 to be inserted into a body cavity, a curved portion 2 which is bent by remote control being connected to a forward end of the flexible tube portion 1, a forward-end-portion body 3 connected to a forward end of the curved portion 2, and an ultrasonic probe 4 attached to the forward-end-portion body 3. The reference numeral 100 designates an inflatable/deflatable balloon which is detachably provided to surround the ultrasonic probe 4.

A curved portion operation knob 6, or the like, for driving the curved portion 2 to bend is disposed in an operation portion 5 connected to a base end of the flexible tube portion 1. The reference numeral 7 designates a treating tool insertion hole through which a treating tool, or the like, is inserted into a treating tool-pass channel 15 disposed in the flexible tube portion 1 so as to be inserted into the flexible tube portion 1.

A video signal connector portion 81 to be connected to a video processor not shown and a light guide connector portion 82 are provided side by side at a forward end of a first connection flexible tube 8 connected to the operation portion 5. An ultrasonic signal connector portion 91 to be connected to an ultrasonic signal processor not shown is provided at a forward end of a second connection flexible tube 9.

Figure 1:
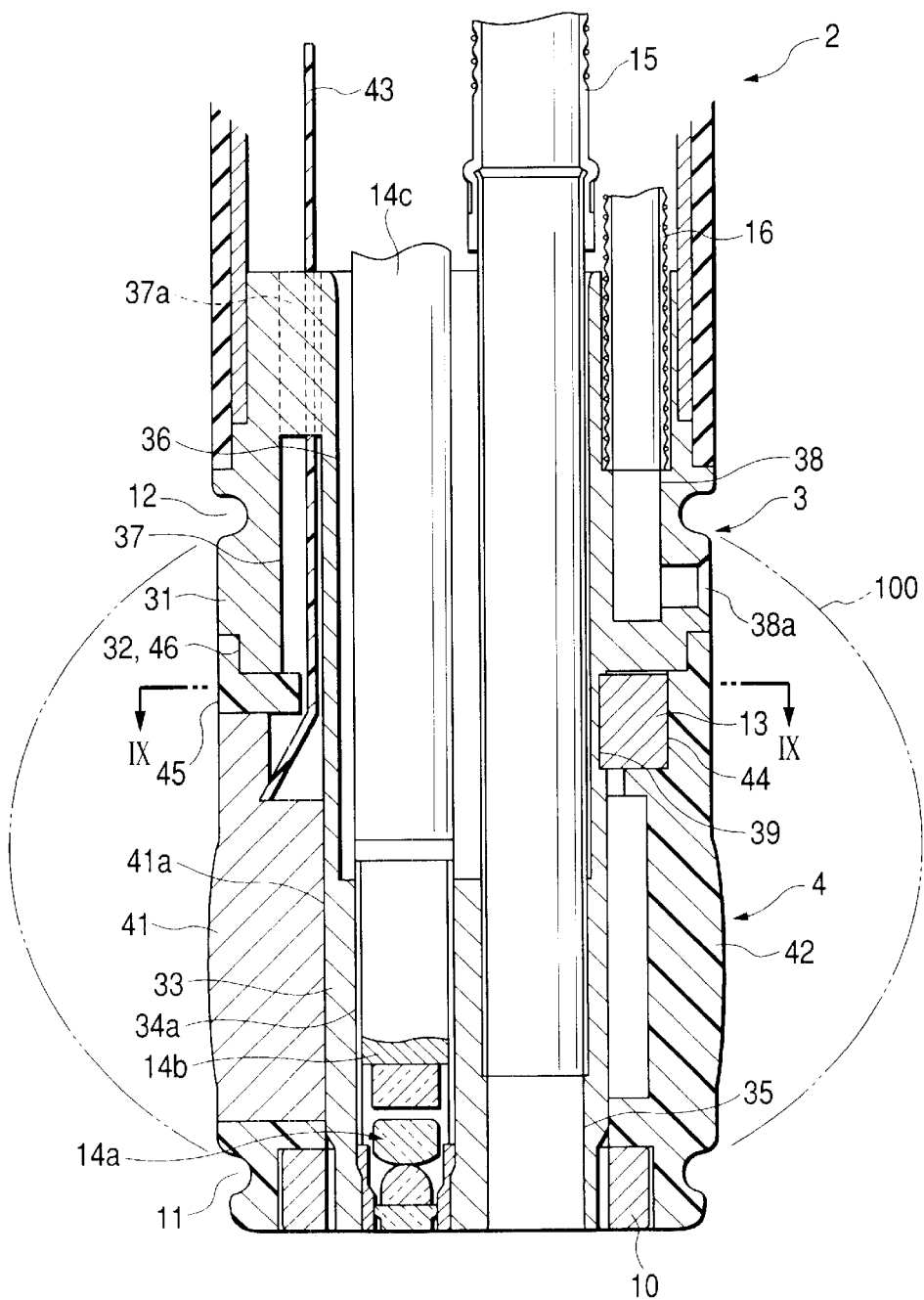
FIG. 1 is a side sectional view of a forward end portion of an insertion portion of an ultrasonic endoscope according to an embodiment of the present invention.

FIG. 1 shows a forward end portion of an insertion portion in which the ultrasonic probe 4 includes an ultrasonic vibrator arrangement portion 41 formed approximately annularly, and a plastic receptacle member 42 for holding the ultrasonic vibrator arrangement portion 41. The ultrasonic vibrator arrangement portion 41 and the receptacle member 42 are integrated into one unit shown in FIG. 3.

Figure 3:
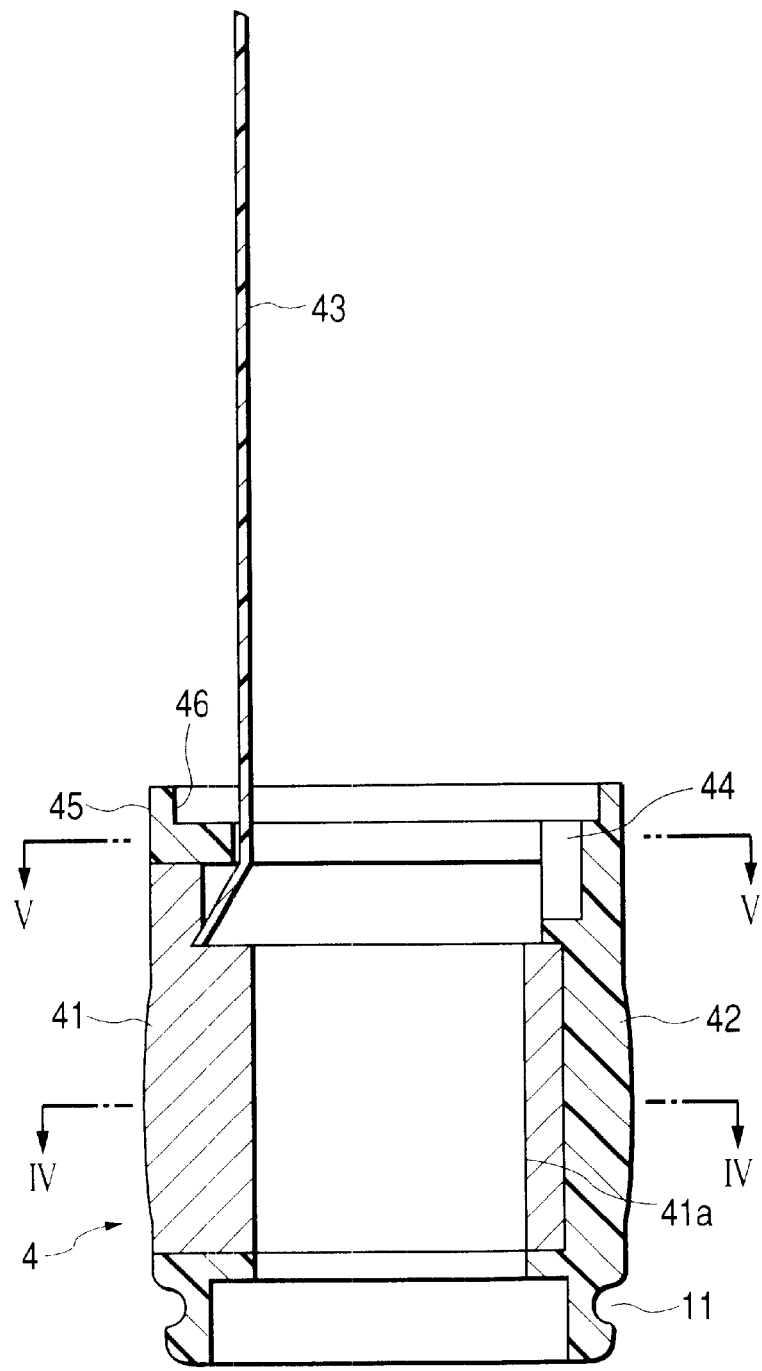
FIG. 3 is a side sectional view of the ultrasonic endoscope according to the embodiment of the present invention.
Figure 4:
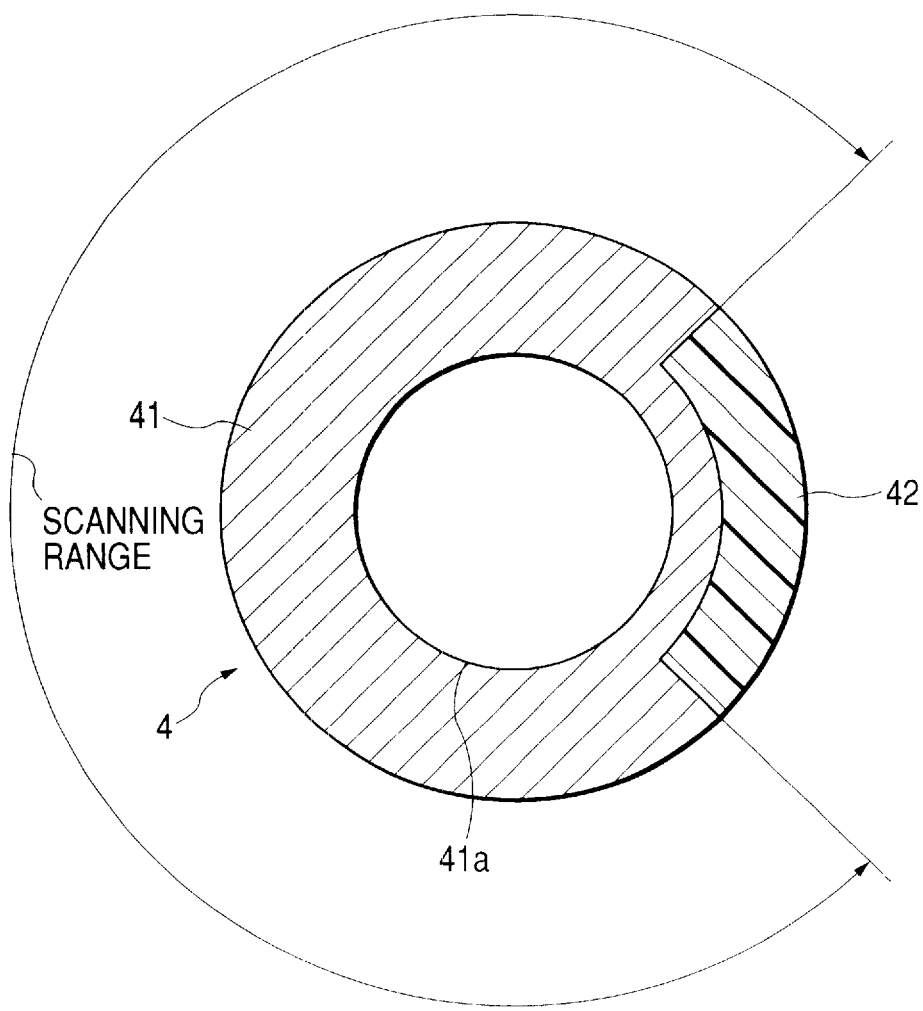
FIG. 4 is a sectional view taken along the line IV—IV in FIG. 3, showing the embodiment of the present invention.

As shown in FIG. 4 which is a sectional view taken along the line IV—IV in FIG. 3, ultrasonic signals are transmitted/received (electronically scanned) successively in a range, for example, of 270°, around an axial line from the ultrasonic vibrator arrangement portion 41 having a large number of ultrasonic vibrators arranged around the axial line. Thus, radial scanning is performed in a direction perpendicular to the axial line.

The inner space of the ultrasonic vibrator arrangement portion 41 is shaped like a cylindrical hole with the axial line as its center. Flexible substrates 43 having wiring for transmitting a signal input into/output from the ultrasonic vibrator arrangement portion 41 are connected to a backward end portion (an upper portion in FIG. 3) of the ultrasonic vibrator arrangement portion 41 so as to extend backward.

Figure 5:
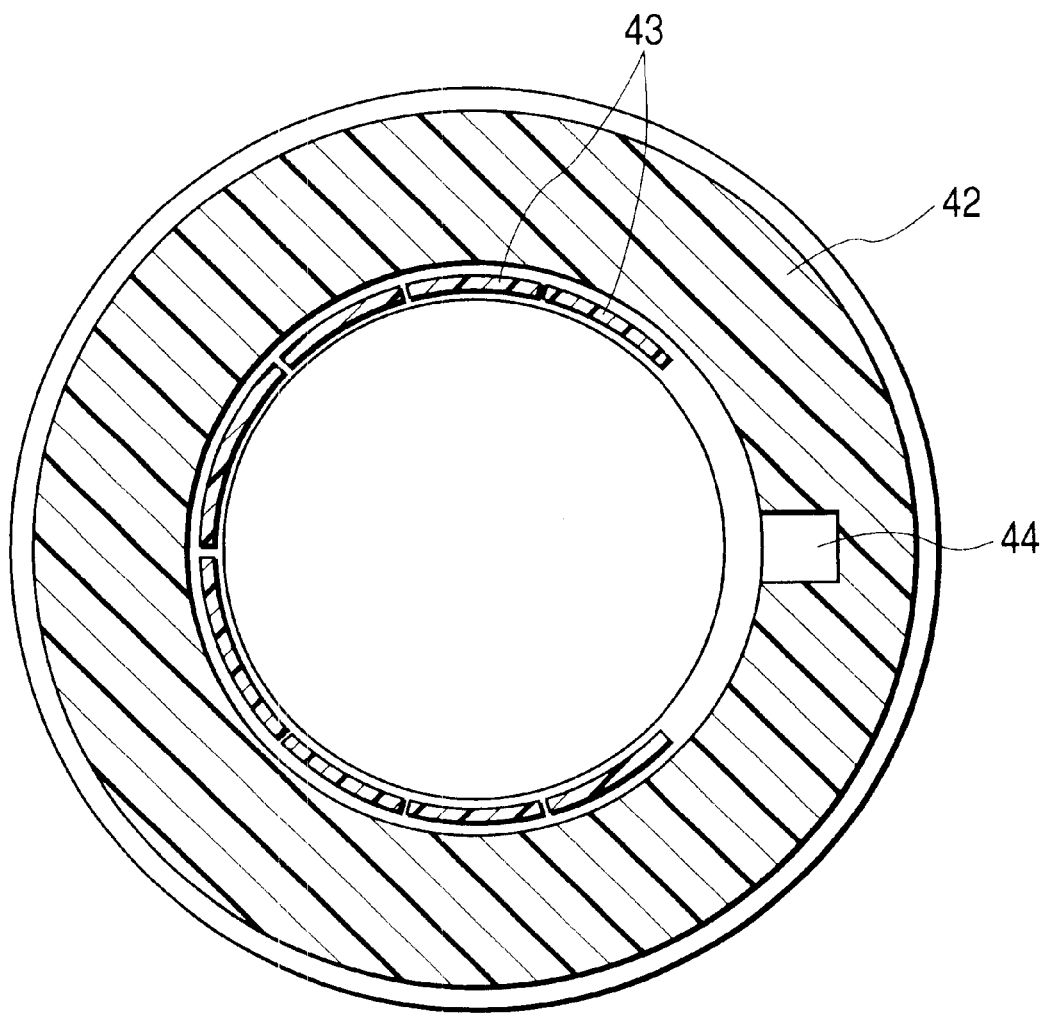
FIG. 5 is a sectional view taken along the line V—V in FIG. 3, showing the embodiment of the present invention.

As shown in FIG. 5 which is a sectional view taken along the line V—V in FIG. 3, the flexible substrates 43 are provided as a plurality of flexible substrates 43 (for example, eight flexible substrates 43), which are provided side by side so as to be shaped like a circular arc around the axial line of the ultrasonic probe 4.

As shown in FIG. 5, the flexible substrates 43 are arranged like a circular arc, for example, in a range of about 270°. A slot 44 for embedding a rotation stopper member 13 which will be described later is formed in a portion which is extension of the circular arc where the flexible substrates 43 are arranged and which has no arrangement of the flexible substrates 43.

Referring back to FIG. 3, a centering fitting portion 46 to be fitted to a centering fitting portion 32 (which will be described later) of the forward-end-portion body 3 is formed in a backward end portion of the receptacle member 42 so as to be concentric with an outer cirumferential surface (an outer circumferential surface of a boundary portion adjacent to the outer surface of the forward-end-portion body 3) 45 in high dimensional accuracy. A circumferential groove 11 for fixing a forward end portion of the inflatable/deflatable balloon 100 by a belt is formed in a forward end portion of the outer circumferential surface of the receptacle member 42.

Figure 6:
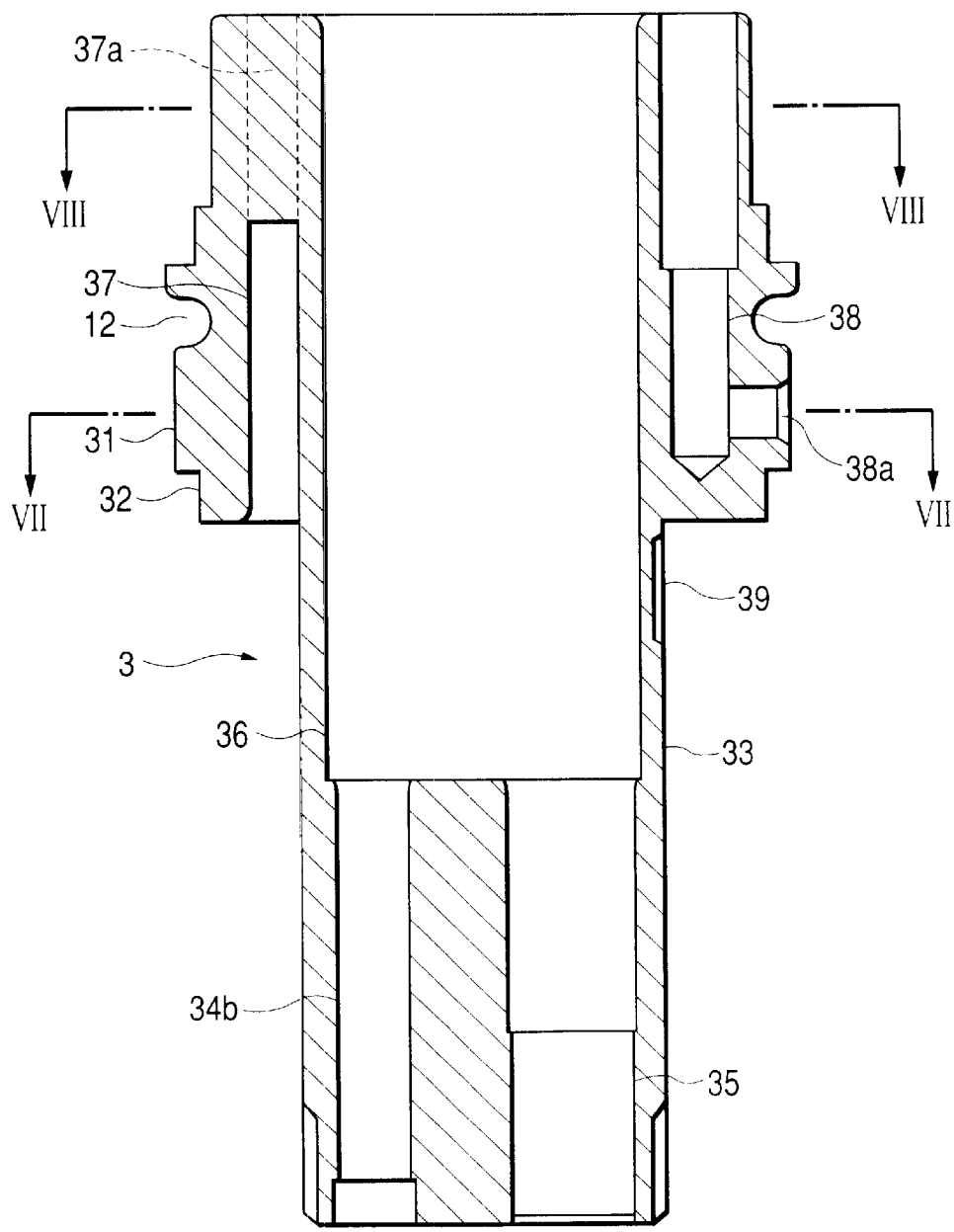
FIG. 6 is a side sectional view of a forward-end-portion body in the embodiment of the present invention.

Referring back to FIG. 1 again, the forward-end-portion body 3 made of a plastic material, or the like, has a forward half portion 33 which is so small in size as to be inserted into an inner circumferential surface 41a of the ultrasonic vibrator arrangement portion 41 of the ultrasonic probe 4 as a single part state of the forward-end-portion body 3 as shown in FIG. 6. Further, an outer circumferential surface 31 of a boundary portion adjacent to the outer circumferential surface of the ultrasonic probe 4 is formed to have the same size as that of the outer circumferential surface 45 of the boundary portion of the ultrasonic probe 4.

A self-aligning fitting portion 32 to be fitted to a self-aligning fitting portion 46 of the ultrasonic probe 4 is formed in a forward end portion of the outer circumferential surface 31 of the boundary portion of the forward-end-portion body 3 so as to be aligned with the outer circumferential surface 31 of the boundary portion in high dimensional accuracy. Further, a circumferential groove 12 for fixing a rear end portion of the balloon 100 by a belt is formed at a backward end of the outer circumferential surface.

An objective arrangement hole 34a, an illumination light guide arrangement hole 34b and a treating tool-pass hole 35 are formed in a forward portion of the forward half portion 33 of the forward-end-portion body 3 so as to be parallel to the axial line. An inclusion-pass hole 36 having an inner diameter slightly smaller than the outer diameter of the forward half portion 33 is formed on the back of the forward portion of the forward half portion 33 so as to extend to a backward end of the forward-end-portion body 3.

Figure 7:
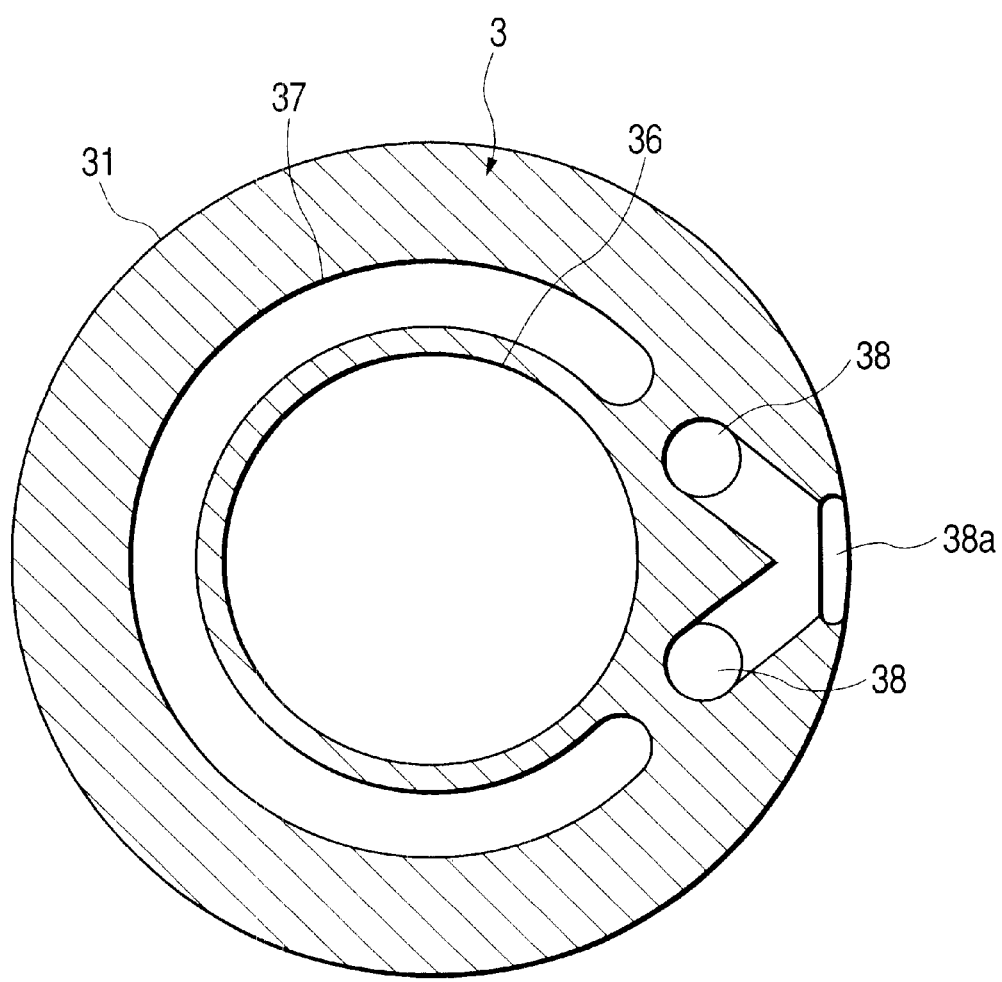
FIG. 7 is a sectional view taken along the line VII—VII in FIG. 6, showing the embodiment of the present invention.

As shown also in FIG. 7 which is a sectional view taken along the line VII—VII in FIG. 6, a flexible substrate-pass hole 37 for making the flexible substrates 43 pass therethrough is formed in a backward half portion of the forward-end-portion body 3 and approximately on a position of extension of the outer circumferential surface of the forward half portion 33 so as to be shaped like a circular arc around the axial line in accordance with the positions of arrangement of the flexible substrates 43.

Figure 8:
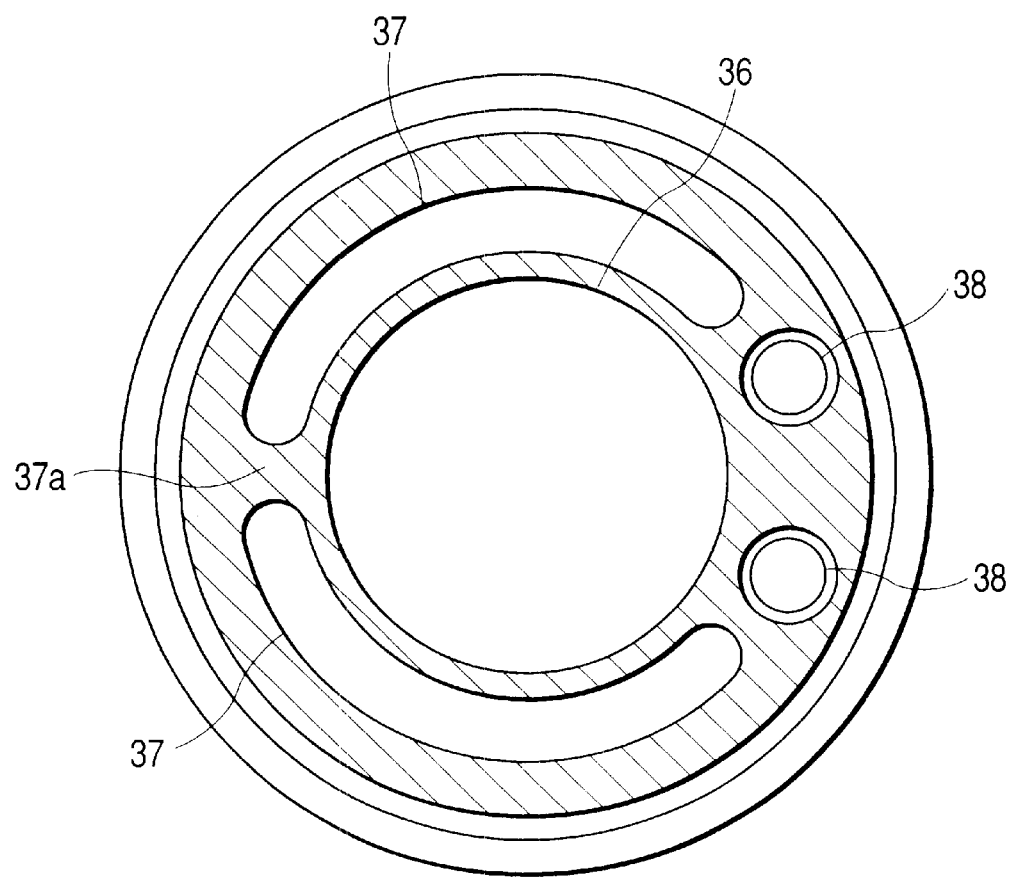
FIG. 8 is a sectional view taken along the line VIII—VIII in FIG. 6, showing the embodiment of the present invention.

Incidentally, as shown in FIG. 8 which is a sectional view taken along the line VIII—VIII in FIG. 6, at least one junction 37a is formed in the middle of the flexible substrate pass hole 37 in the vicinity of the backward end portion of the forward-end-portion body 3 so that the flexible substrate-pass hole 37 is divided into two by the junction 37a to thereby ensure strength sufficient to prevent the forward-end-portion body 3 from being squashed by external force.

Referring back to FIGS. 6 and 7, the flexible substrate-pass hole 37 is shaped like a circular arc in a range of about 280°. Fluid passages 38 for injecting degassing water into the balloon 100 and discharging degassing water from the balloon 100 respectively are formed in a portion in which the flexible substrate-pass hole 37 is not formed. The fluid passages 38 are formed in parallel to the axial line so as to communicate with a balloon communication opening 38a opened into the balloon 100.

The two fluid passages 38 are formed side by side. One of the two fluid passages 38 is used for discharging degassing water and gas. Although the fluid passages 38 do not appear in FIG. 6 (and in FIG. 1) originally, the fluid passages 38 are shown in FIG. 6 (and in FIG. 1) to facilitate an understanding of the description. The reference numeral 39 designates a slot for embedding a rotation stopper member 13.

Referring back to FIG. 1, the ultrasonic probe 4 fitted to the forward half portion 33 of the forward-end-portion body 3 is pressed and fixed to an intermediate stepped surface of the forward-end-portion body 3 by a nut member 10 to be thread-engaged with a male screw formed on the outer circumference of the forward end portion of the forward-end-portion body 3.

Figure 9:
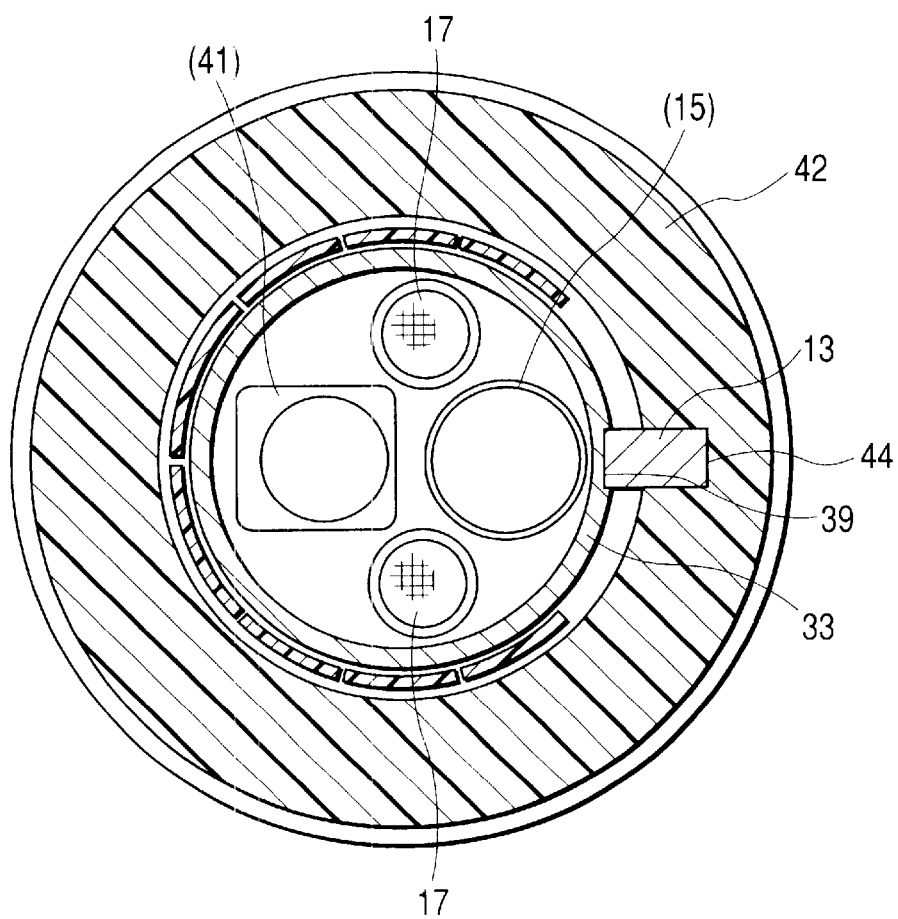
FIG. 9 is a sectional view taken along the line IX—IX in FIG. 1, showing the embodiment of the present invention.

As shown also in FIG. 9 which is a sectional view taken along the line IX—IX in FIG. 1, the rotation stopper member 13 shaped like a rectangular parallelepiped is embedded in the slot 44 of the ultrasonic probe 4 and in the slot 39 of the forward-end portion-body 3 to thereby limit positioning in the direction of rotation of the ultrasonic probe 4 relative to the forward-end-portion body 3. Hence, the relation between the direction of ultrasonic scanning and the direction of observation view field is set correctly. The reference numeral 17 designates illumination light guide fibers.

Referring back to FIG. 1 again, in the state where the ultrasonic probe 4 is fixed to the forward-end-portion body 3, the forward half portion 33 of the forward-end-portion body 3 and the inner circumferential surface 41a of the ultrasonic vibrator arrangement portion 41 are fitted to each other and the centering fitting portion 32 of the forward-end-portion body 3 and the centering fitting portion 46 of the ultrasonic probe 4 are fitted to each other. The gap between the former fitting portions is formed so as to be larger than the gap between the latter fitting portions.

As a result, it is seldom that there occurs a difference in level in the joint portion which is one of joint portions between the forward-end-portion body 3 and the ultrasonic probe 4 and which is between the boundary portion outer circumferential surface 31 of the forward-end-portion body 3 and the boundary portion outer circumferential surface 45 of the ultrasonic probe 4. Thus, a forward end portion having a good property for insertion into a patient is formed.

An objective optical system 14a is disposed in a forward portion of the objective arrangement hole 34. A solid image-pickup device 14b is disposed in a backward portion of the objective arrangement hole 34. A signal cable 14c for transmitting an image-pickup signal, or the like, passes through the inside of the inclusion-pass hole 36 and extends backward into the curved portion 2. A treating tool insertion channel 15 is connected to the treating tool-pass hole 35 through a stainless steel pipe.

Flexible piping tubes 16 are connected to the two fluid passages 38 respectively. The balloon 100 has opposite ends fixed to the circumferential grooves 11 and 12 respectively. Hence, degassing water can be injected into the balloon 100 and discharged from the balloon 100 through the piping tubes 16 by control from the operation portion 5 so that the balloon 100 can be inflated/deflated.

As shown in FIG. 1, the flexible substrates 43 for transmitting a signal inputted into or outputted from the ultrasonic vibrator arrangement portion 41 are drawn backward into the curved portion 2 via the flexible substrate-pass hole 37 formed in the forward-end-portion body 3.

Figure 10:
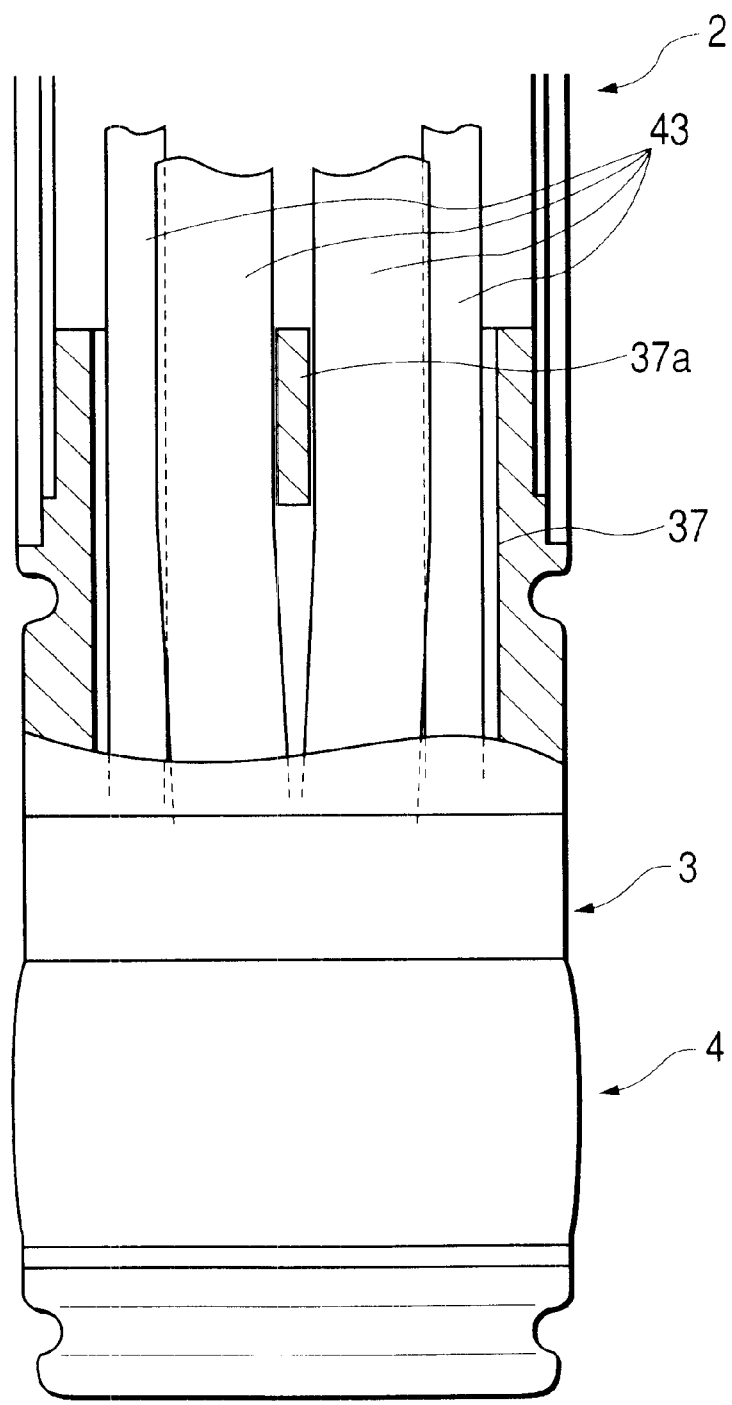
FIG. 10 is a partly sectional view showing a state of passage of flexible substrates in the embodiment of the present invention.

As shown in FIG. 10, in the backward half portion of the flexible substrate-pass hole 37, the flexible substrates 43 are disposed so that the flexible substrates 43 are drawn backward into the curved portion 2 while adjacent flexible substrates 43 slightly overlap each other in order to avoid interference with the junction 37a.

In the curved portion 2, all the signals inputted into or outputted from the ultrasonic vibrator arrangement portion 41 are transmitted by wiring formed in the thin flexible substrates 43. Hence, a signal cable, or the like, need not be inserted/disposed in the curved portion 2.

The flexible substrates 43 are arranged like a circular arc surrounding various inclusions such as the signal cable 14c of the solid image-pickup device 14b, the treating tool insertion channel 5 and the light guide fibers 17. Hence, various inclusions are inserted/disposed in the curved portion 2 without any wasteful inner space, so that the curved portion 2 can be formed so as to be small in size.

As shown in FIG. 11, the flexible substrates 43 are formed to have different lengths respectively. Even the shortest flexible substrate 43 is set to have a length sufficient to pass through the inside of the curved portion 2. The signal cable 47 inserted/disposed in the flexible tube portion 1 has signal wires 47a. The flexible substrates 43 are connected to forward ends of the signal wires 47a respectively while the flexible substrates 43 are displaced successively in the direction of the length of the signal cable 47.

Portions of connection of the flexible substrates 43 to the signal wires 47a of the signal cable 47 are enlarged in diameter by soldering, or the like. Local enlargement can be, however, avoided totally because the portions are displaced successively. Hence, the flexible tube portion 1 and the curved portion 2 can be formed to be small in size.

FIG. 12 shows such connection portions disposed in the inside of the flexible tube portion 1. A forward end portion of the signal cable 47 having a large number of signal wires 47a bound into one is disentangled into individual signal wires 47a in the inside of the flexible tube portion 1. Groups of signal wires 47a which are to be connected to corresponding flexible substrates 43. Each group of signal wires 47a are covered with a flexible heat-shrinkable tube 48 and bundled into one. Such configuration has a good effect on preventing the respective signal wires 47a from being broken.

The respective heat-shrinkable tubes 48 are disposed while end portions of the heat-shrinkable tubes 48 are displaced successively. Hence, the flexibility of the flexible tube portion 1 does not change rapidly, so that the change of the diameter of the flexible tube portion as a whole is smoothened to thereby avoid the enlargement of the diameter. Further, the respective end portions of the heat-shrinkable tubes 48 are covered with a flexible large-diameter heat-shrinkable tube 49 so that the respective end portions are bound into one as a whole.

According to the present invention, a plurality of flexible substrates as a signal transmission member for transmitting a signal input into/output from an ultrasonic probe are connected to the ultrasonic probe and drawn into a curved portion so that the plurality of flexible substrates are connected to a signal cable at lengthwise different positions in a flexible tube portion. Hence, an inner space near a forward end of an insertion portion is used so effectively that the signal transmission member can be inserted/disposed in the inner space and that improvement of insertion characteristic can be attained by reduction in the outer diameter of the insertion portion.

According to the present invention, a signal cable including signal wires and disposed so as to be inserted into a flexible tube portion is connected to an ultrasonic probe by a plurality of flexible substrates disposed side by side so as to pass through the inside of a curved portion. A plurality of signal wires connected to one and the same of the flexible substrate, among the signal wires drawn out from the signal cable, are bound up into one as a bundle in the connection portion between the flexible substrates and the signal cable. Hence, an inner space near a forward end of an insertion portion is used so effectively that the flexible substrates can be arranged so as to be connected to the signal cable and that improvement of insertion property can be attained by reduction in the outer diameter of the insertion portion.

What is claimed is:

1. An ultrasonic endoscope comprising a flexible tube portion forming an insertion portion, a curved portion connected to a forward end of said flexible tube portion so as to be bent by remote control, an ultrasonic probe for transmitting and receiving an ultrasonic signal, and an objective optical system for making optical observation, said probe and said objective optical system being disposed in a further forward position than said curved portion, wherein a plurality of flexible substrates are connected to said ultrasonic probe as a signal transmission member for transmitting a signal which is inputted into/outputted from said ultrasonic probe, said plurality of flexible substrates being drawn into said curved portion and connected to a signal cable at lengthwise different positions respectively in the inside of said flexible tube portion.

2. The ultrasonic endoscope according to claim 1, wherein said plurality of flexible substrates are arranged in the inside of said curved portion so as to be shaped like a circular arc surrounding other inclusions.

3. An ultrasonic endoscope comprising a flexible tube portion forming an insertion portion, a curved portion connected to a forward end of said flexible tube portion so as to be bent by remote control, an ultrasonic probe for transmitting and receiving an ultrasonic signal, and an objective optical system for making optical observation, said probe and said objective optical system being disposed in a further forward position than said curved portion, wherein a signal cable including signal wires and disposed so as to be inserted into said flexible tube portion is connected to said ultrasonic probe by a plurality of flexible substrates disposed side by side so as to pass through the inside of said curved portion, and a plurality of signal wires connected to one and the same flexible substrate, among said signal wires drawn out from said signal cable, are bound up into one as a bundle in the connection portion between the flexible substrates and the signal cable.

4. The ultrasonic endoscope according to claim 3, wherein each of said bundles of said signal wires is made by being covered with a flexible tube.

5. The ultrasonic endoscope according to claim 3, wherein said bundles of signal wires are formed by displacement from one another in an axial direction.

6. An ultrasonic endoscope comprising:

a flexible tube portion;

a forward end portion body having an ultrasonic probe;

a curved portion connecting the flexible tube portion to the forward end portion body, and operatively bendable to vary an angle of the forward end portion body with respect to the flexible tube portion;

a plurality of flexible substrates extending from the forward end portion body to the flexible tube portion and passing through the curved portion, wherein the flexible substrates are arranged circumferentially at least within the curved portion, one ends of the flexible substrates are connected to the ultrasonic probe within the forward end portion body, and the flexible substrates can be at least partially overlapped with one another; and a signal cable having signal wires that are connected to the other ends of the flexible substrates within the flexible tube portion.

7. The ultrasonic endoscope according to claim 6, wherein the signal wires are connected to the other ends of the flexible substrates at different locations in a lengthwise direction.

8. The ultrasonic endoscope according to claim 6, wherein the signal wires are bundled into a plurality of groups corresponding respectively to the plurality of the flexible substrates.

9. The ultrasonic endoscope according to claim 8, wherein the signal wires are bundled by heat shrinkable tubes.

10. The ultrasonic endoscope according to claim 6, wherein each of the flexible substrate is in the form of a strip.

* * * * *